(12) United States Patent
Joshi

(10) Patent No.: US 10,383,832 B1
(45) Date of Patent: *Aug. 20, 2019

(54) SUSTAINED RELEASE METOPROLOL FORMULATIONS

(71) Applicant: CMax Technologies, Inc., Markham (CA)

(72) Inventor: Laxminarayan Joshi, Markham (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/390,469

(22) Filed: Dec. 24, 2016

Related U.S. Application Data

(63) Continuation of application No. 14/612,508, filed on Feb. 3, 2015, now Pat. No. 9,561,187.

(60) Provisional application No. 61/935,080, filed on Feb. 3, 2014.

(51) Int. Cl.
| | | |
|---|---|---|
| *A61K 9/00* | (2006.01) | |
| *A61K 9/20* | (2006.01) | |
| *A61K 31/138* | (2006.01) | |
| *A61K 9/28* | (2006.01) | |

(52) U.S. Cl.
CPC .......... *A61K 31/138* (2013.01); *A61K 9/2009* (2013.01); *A61K 9/2013* (2013.01); *A61K 9/2018* (2013.01); *A61K 9/2027* (2013.01); *A61K 9/2031* (2013.01); *A61K 9/2054* (2013.01); *A61K 9/2059* (2013.01); *A61K 9/2077* (2013.01); *A61K 9/2095* (2013.01); *A61K 9/28* (2013.01); *A61K 9/2893* (2013.01)

(58) Field of Classification Search
CPC .. A61K 9/2059; A61K 9/2009; A61K 9/2013; A61K 9/2018; A61K 9/2027; A61K 9/2031; A61K 9/2054; A61K 31/138
See application file for complete search history.

(56) References Cited

U.S. PATENT DOCUMENTS

| | | | |
|---|---|---|---|
| 2007/0042951 A1* | 2/2007 | Olejnik | A61K 9/0048 548/300.1 |
| 2007/0053983 A1* | 3/2007 | Jain | A61K 9/205 424/486 |
| 2008/0193530 A1* | 8/2008 | Blackburn | A61K 9/0019 424/468 |
| 2013/0202705 A1* | 8/2013 | Hamed | A61K 9/2027 424/488 |

OTHER PUBLICATIONS

Fini et al., "Fast dispersible / slow releasing ibuprofen tablets", European Journal of Pharmaceutics and Biopharmaceutics 69 (2008) 335-341. (Year: 2008).*

* cited by examiner

*Primary Examiner* — Jianfeng Song

(57) ABSTRACT

The present invention relates to modified release pharmaceutical composition comprising metoprolol succinate, one or more release modifying agent(s) and one or more pharmaceutically acceptable excipient(s). More specifically, the invention relates to modified release pharmaceutical compositions comprising metoprolol succinate and a process for preparation thereof.

14 Claims, No Drawings

SUSTAINED RELEASE METOPROLOL FORMULATIONS

FIELD OF THE INVENTION

This present invention relates to modified release pharmaceutical composition comprising metoprolol succinate, one or more release modifying agent(s) and one or more pharmaceutically acceptable excipient(s). More specifically, the invention relates to modified release pharmaceutical compositions comprising metoprolol succinate and a process for preparation thereof.

BACKGROUND OF THE INVENTION

Metoprolol is a beta$_1$-selective (cardioselective) adrenoceptor blocking agent, available as immediate and extended-release tablets as well as for injection. Examples of beta-adrenergic blockers include propanolol (Inderal, Inderal LA, Innopran XL), atenolol (Tenormin), and timolol (Blocadren). Metoprolol blocks the action of the sympathetic (involuntary) nervous system by blocking beta receptors on sympathetic nerves. Since the sympathetic nervous system is responsible for increasing the rate with which the heart beats, by blocking the action of these nerves metoprolol reduces the heart rate and is useful in treating abnormally rapid heart rhythms.

Metoprolol is selective, moderately lipophilic, without intrinsic sympathomimetic activity, has weak membrane stabilizing activity, and has a short half-life, and therefore must be taken at least twice daily or as a slow-release preparation.

TOPROL-XL® is an extended-release tablet of metoprolol succinate sold by Astra Zeneca and intended for once daily administration. TOPROL-XL® has been formulated to provide a controlled and predictable release of metoprolol for once-daily administration. The tablets comprise a multiple unit system containing metoprolol succinate in a multitude of controlled release pellets. Each pellet acts as a separate drug delivery unit and is designed to deliver metoprolol continuously over the dosage interval. Its chemical name is (±)1(isopropylamino)-3-[p-(2-methoxyethyl) phenoxy]-2-propanol succinate (2:1) (salt). Inactive Ingredients in Toprol XL® include silicon dioxide, sodium stearyl fumarate, polyethylene glycols, titanium dioxide, paraffin, and hypromethylcellulloses. (Toprol XL® label).

Metoprolol tartrate is available in the USA as immediate release tablets for oral administration and in ampuls for intravenous administration. Each ampul contains a sterile solution of metoprolol tartrate, sodium chloride, and water for injection. Metoprolol tartrate is (±)-1-(Isopropylamino)-3-[p-(2-methoxyethyl)phenoxy]-2-propanol L-(+)-tartrate (2:1) salt.

Metoprolol has a very low melting point, tartrate around 120° C., succinate around 136° C. Because of this, metoprolol is always manufactured in a salt-based solution, as drugs with low melting points are difficult to work with in a manufacturing environment. The free base exists as a waxy white solid, and the tartrate salt is finer crystalline material. Metoprolol is metabolized in the liver to inactive metabolite and undergoes a-hydroxylation and O-demethylation as a substrate of the cytochrome liver enzymes CYP2D6 and a small percentage by CYP3A4.

Metoprolol succinate is a white crystalline powder with a molecular weight of 652.8. Metoprolol succinate is a classic example of a BCS (Biopharmaceutics Classification System) class 1 drug which is highly soluble and has high permeability and is well absorbed and its absorption rate is higher than excretion. It is freely soluble in water; soluble in methanol; sparingly soluble in ethanol; slightly soluble in dichloromethane and 2-propanol; practically insoluble in ethyl-acetate, acetone, diethylether and heptane.

Metoprolol tartrate is a white, practically odorless, crystalline powder with a molecular weight of 684.82. It is very soluble in water; freely soluble in methylene chloride, in chloroform, and in alcohol; slightly soluble in acetone; and insoluble in ether.

Metoprolol reduces the force of contraction of heart muscle and thereby lowers blood pressure. By reducing the heart rate and the force of muscle contraction, metoprolol reduces the need for oxygen by heart muscle. Since heart pain (angina pectoris) occurs when oxygen demand of the heart muscle exceeds the supply of oxygen, metoprolol, by reducing the demand for oxygen, is helpful in treating heart pain Metoprolol succinate is indicated for the treatment of hypertension, to lower blood pressure. Lowering blood pressure lowers the risk of fatal and non-fatal cardiovascular events, primarily strokes and myocardial infarctions. These benefits have been seen in controlled trials of antihypertensive drugs from a wide variety of pharmacologic classes including metoprolol.

Numerous antihypertensive drugs, from a variety of pharmacologic classes and with different mechanisms of action, have been shown in randomized controlled trials to reduce cardiovascular morbidity and mortality, and it can be concluded that it is blood pressure reduction, and not some other pharmacologic property of the drugs, that is largely responsible for those benefits. The largest and most consistent cardiovascular outcome benefit has been a reduction in the risk of stroke, but reductions in myocardial infarction and cardiovascular mortality also have been seen regularly. Elevated systolic or diastolic pressure causes increased cardiovascular risk, and the absolute risk increase per mmHg is greater at higher blood pressures, so that even modest reductions of severe hypertension can provide substantial benefit. Relative risk reduction from blood pressure reduction is similar across populations with varying absolute risk, so the absolute benefit is greater in patients who are at higher risk independent of their hypertension (for example, patients with diabetes or hyperlipidemia), and such patients would be expected to benefit from more aggressive treatment to a lower blood pressure goal. Metoprolol succinate may be administered with other antihypertensive agents.

Metoprolol succinate is also indicated in the long-term treatment of angina pectoris, to reduce angina attacks and to improve exercise tolerance. Metoprolol succinate is also indicated for the treatment of stable, symptomatic (NYHA Class II or III) heart failure of ischemic, hypertensive, or cardiomyopathic origin. It was studied in patients already receiving ACE inhibitors, diuretics, and, in the majority of cases, digitalis. In this population, Metoprolol succinate decreased the rate of mortality plus hospitalization, largely through a reduction in cardiovascular mortality and hospitalizations for heart failure.

Metoprolol is marketed under the brand name Lopressor® by Novartis, and Toprol-XL® by AstraZeneca (in the USA); Selokeen® (in the Netherlands); as Minax® by Alphapharm (in Australia), Metrol® by Arrow Pharmaceuticals (in Australia), as Betaloc® by AstraZeneca, as Bloxan® by Krka (company) (in Slovenia), as Neobloc® by Unipharm (in Israel), Presolol® by Hemofarm (in Serbia) and as Corvitol® by Berlin-Chemie AG (in Germany). In India, this drug is available under the brand names of Met-XL®, Metolar® and Starpress, Restopress®.

Controlled-release formulations have been one of the major focuses in pharmaceutical research and development. Matrix systems are a very attractive approach in controlled-release systems.

The advantages of controlled release products are well known in the pharmaceutical field. Sustained release drug formulations may be useful to reduce the frequency of drug administration (especially in the case of drugs with short compound half lives such as metoprolol), improve patient compliance, reduce drug toxicity (local or systemic associated with high peak exposure), reduce drug level fluctuation in blood, stabilize medical condition with more uniform drug levels, reduce drug accumulation with chronic therapy, improve bioavailability of some drugs because of spatial control, and reduce total drug usage when compared with immediate release drugs.

Mechanical devices aside, interaction between a drug and a polymeric material usually forms the basis of controlled oral drug delivery. A polymer at certain concentrations in a solution imposes pathways for drug diffusion. Polymers that dissolve in or otherwise hydrate in aqueous media can alter the drug diffusion process in a time-dependent manner. For example, a commonly used material, hydroxypropyl methylcellulose (HPMC), which is water soluble, behaves as a swellable absorptive polymer in the limited volumes of aqueous media in the gastrointestinal tract. Drug dispersed in this polymer, as in monolithic tablets, diffuses through the viscous hydrated polymer at a rate dependent on the movement kinetics of the polymer chains. The faster these relax, the faster the diffusion rate.

Development of dosage form depends on chemical nature of the drug and polymers, the matrix structure, swelling, diffusion, erosion, the release mechanism and the in vivo environment.

Hydrophilic polymers like HPMC may also control drug release by erosion mechanisms. After consumption of the dosage form, the GI tract fluid encounters the dosage unit, causing the polymer to hydrate and swell. Weakened mechanical properties in the swollen state may cause the hydrated polymer to break away from the prime particle (compact or pellet). Drug release may therefore be controlled by a combination of diffusion and erosion. Such release mechanisms can apply to systems where drug is dispersed in or coated with polymer.

Delivery to specific regions of the GI tract may be achieved using polymers with pH-dependent solubilities. These include enteric polymers with carboxylic acid functional groups; their pH-dependent solubility determines location for release.

Water insoluble polymers can extend drug release. These include methacrylate- or acrylate-based polymers with low permeability.

Hydrophilic functional groups such as trimethylaminoethyl methacrylate can improve permeability and swellability in water thus altering release behaviors. Technologies have been developed to exploit diffusion, erosion, and other physicochemical mechanisms and provide drug and disease-specific release profiles. Examples include the release from a Contramid™ tablet controlled by the degree of crosslinking of high amylase starch and Alza's Oros™ and Duros™ technologies are based on osmosis-driven release.

Different hydrogels have been described for use in controlled release medicines, most of which are semi-synthetic or of natural origin. A few contain both synthetic and non-synthetic material. However, many of the systems require special process and production equipment, and in addition some of these systems are susceptible to variable drug release.

Oral controlled release delivery systems should ideally be adaptable so that release rates and profiles can be matched to physiological and temporal requirements. While many controlled and sustained-release formulations are already known, certain soluble to highly soluble drugs present formulation difficulties when included in such formulation. An example of such a highly soluble drug is metoprolol. There have been a number of patents in the prior art which relate to controlled release metoprolol formulations and yet the successful extended release versions of metoprolol succinate currently consist of complex, expensive multiparticulate formulations such as that of Toprol XL®.

U.S. Pat. No. 5,169,638 describes a buoyant controlled release pharmaceutical formulation in the form of a powder filled capsule in which an active ingredient of a basic character exhibits a pH-independent controlled release. The powder comprises the active agent, which may be metoprolol, a water-soluble salt of polyuronic acid, a pH-independent hydrocolloid gelling agent (e.g., hydroxypropylmethylcellulose, methylcellulose or hydroxypropylcellulose), and a binder (HPMC). The formulation is free of calcium ion and carbon dioxide producing material and is said to float gastric juices so that it will have extended residence time in the stomach in contrast to the instant invention which preferably provides colonic release.

U.S. Pat. No. 5,399,362 describes a sustained release oral solid dosage form of metoprolol including a gelling agent, an inert pharmaceutical diluent, a cationic cross-linking agent. The formulation provides release of metoprolol for at least about 24 hours.

U.S. Pat. No. 4,957,745 also describes a controlled release metoprolol. The preparation includes a plurality of beads comprising metoprolol coated with a polymeric membrane comprising ethylcellulose with or without hydroxypropylmethylcellulose.

U.S. Pat. No. 4,871,549 describes a time controlled explosion system comprising metoprolol, a swelling agent such as a low substituted hydroxypropylcellulose, sodium starch glycolate or carboxymethylcellulose sodium, coated with a water-insoluble coating material so that drug release is caused by the explosion of the membrane after a definite time period.

U.S. Pat. No. 5,081,154 is directed to metoprolol succinate in an oral composition coated with an anionic polymer soluble at pH over 5.5 and a water insoluble quaternary ammonium substituted acrylic polymer.

U.S. Pat. No. 4,792,452 describes controlled release pharmaceutical compositions which are said to provide pH-independent release for a basic drug such as metoprolol. The formulations include a pH-dependent polymer which is a salt of alginic acid, a pH-independent hydrocolloid gelling agent and a binder. The salt of the alginic acid is preferably sodium alginate or potassium alginate. The weight ratio of the alginic acid salt to the hydrocolloid gelling agent is all within the range 0.1:1 to 10:1, and the formulation is free of calcium ion and carbon dioxide-producing material.

There is a metoprolol formulation marketed in the United Kingdom called Betaloc®S.A., which contains 200 mg of metoprolol tartrate in a controlled release matrix. Metoprolol is available as 50 mg, 100 mg and 200 mg extended release tablets in the United States and is marketed under the name Toprol XL® from AstraZeneca. Toprol XL® tablets contain the succinate salt of metoprolol (equivalent to 50 mg, 100 mg and tablets comprise a multiple unit system containing metoprolol succinate in a multitude of controlled release pellets. These tablets may be dosed once daily. Studies have shown that formulations similar to those of Toprol XL®, containing metoprolol succinate in a multitude of controlled release pellets, has a more sustained time profile of beta-blockade at steady-state than formulations similar to those of Betaloc® SA., containing metoprolol tartrate in a controlled release matrix. See, e.g., Berend Oosterhuis, PhD, et al., "A Pharmacokinetic and Pharmacodynamic Comparison of Metoprolol CR ZOK with a Conventional Slow Release Preparation," J Clin. Pharmacol., 1990:30:533-538. Additionally, these studies have shown that metoprolol succinate in an extended release form similar to Toprol XL® had mean and individual plasma concentration-time profiles that were said to be smoother than the profiles of formulations such as those of Betaloc® S.A. Further, for formulations containing metoprolol succinate in a controlled release form similar to Toprol XL®, the value of $C_{max}$ was significantly lower, the $C_{mm}$ was higher, the $T_{max}$ value tended to be longer, and the time during which the metoprolol plasma concentration exceeded 75% of $C_{max}$ was significantly longer versus formulations, similar to those of Betaloc®S.A. containing metoprolol tartrate in a controlled release matrix.

Furthermore, the process employed to create the multitude of controlled-release pellets of Toprol XL® is more complex and time consuming than a monolithic matrix formulation.

In the USA, Metoprolol tartrate (Lopressor) is a regular, immediate-release tablet, while metoprolol succinate (Toprol XL®) is an extended-release tablet. A shortage of generic metoprolol succinate has necessitated switching some patients to alternative therapy. An option for some patients is metoprolol tartrate (Lopressor and its generics) but there are differences between metoprolol tartrate and metoprolol succinate. Metoprolol tartrate is usually dosed twice daily. It can be effective for hypertension when dosed once daily, but low doses (e.g., 100 mg) given once daily may not control blood pressure for a full 24 hours. Metoprolol succinate is dosed once daily. Metoprolol succinate produces more level metoprolol concentrations than the immediate-release tablets (i.e., lower peaks and less peak-to-trough variation). Metoprolol tartrate is at least 30% more bioavailable than metoprolol succinate (i.e., more drug is absorbed). However, overall 24 hour betablockade is comparable at the same dose. PHARMACISTS LETTER/PRESCRIBER'S LETTER March 2009~Volume 25~Number 250302

Accordingly, there exists a need in the art to provide a monolithic, matrix-based sustained release oral dosage form that provides for the sustained release of metoprolol succinate suitable for once-a-day administration.

SUMMARY OF THE INVENTION

The present invention, is directed to a sustained release oral monolithic starch acetate containing tablets comprising a therapeutically effective amount of metoprolol succinate, and sustained release excipients.

The present invention, is further directed to extended-release drug composition comprising a monolithic matrix tablet comprising metoprolol containing granules and extragranular excipients wherein the granules comprise about:
  20-30% metoprolol succinate;
  5-10% dibasic calcium phosphate;
  5-10% lactose monohydrate;
  5-10% pregelatinized modified starch; and
  1-5% hydroxyl ethyl cellulose; and where the extragranular excipients comprise about:
  5-15% carbomer homopolymer;
  5-15% polyethylene oxide;
  10-20% hypromellose; and
  5-10% methacrylic acid copolymer.

DETAILED DESCRIPTION

Extending drug release (sustained release) from a dosage form can prolong its action and attenuate peak plasma levels, thereby obviating concentration-related side effects or optimize efficacy by matching systemic presence with other time-related effects. Sustained release drug forms can be achieved by embedding the drug in a matrix that prevents immediate release and delivers excipient at a desired rate consistent with absorption or disposition requirements. A wide variety of materials can be used to design the most appropriate release profile and provide a viable and consistent mode of manufacture.

Metoprolol succinate is a class I drug which is high soluble and high permeable. In terms of difficulty it is more difficult to control drug release of metoprolol due to its high aqueous solubility. There is a reverse mechanism of drug release in the delivery system, in this invention we retard drug release from metoprolol succinate by using different grades of rate controlling polymer in conjunction with starch acetate. The drug release mechanism from the drug form of the instant invention follows diffusion in the initial hours and erosion in later stages of delivery. This allows a simple, cost effective approach to achieving bioequivalence with the more complex delivery mechanism of TOPROL-XL®.

TOPROL-XL® is an extended-release tablet of metoprolol succinate is intended for once daily administration. TOPROL-XL® has been formulated to provide a controlled and predictable release of metoprolol for once-daily administration. The tablets comprise a multiple unit system containing metoprolol succinate in a multitude of controlled release pellets. Each pellet acts as a separate drug delivery unit and is designed to deliver metoprolol continuously over the dosage interval.

Matrix-based sustained release systems may incorporate monolithic matrix systems or coating systems. Monolithic matrix systems include a release-controlling polymer matrix containing dispersed or dissolved drug. Either hydrophilic or insoluble matrix systems may be used. Coated systems include a drug-containing core enclosed within a polymer barrier coat. These coating systems can be simple diffusion/erosion systems or osmotic systems where the drug core is contained within a semipermeable polymer membrane with a mechanical/laser drilled hole for drug release, driven by osmotic pressure generated within the tablet core. See, for example, Cao et al., J. Controlled Release, 108:351-361 (2005); Pillay, U.S. Pat. No. 6,090,411.

Drug embedded matrix tablets are one of the least complicated approaches for obtaining controlled release and are widely used and preferred when achievable. Polymers and release retarding materials used as matrix formers in matrix tablets play a vital role in controlling the drug release from the tablets. Though a variety of polymeric materials are available to serve as release retarding matrix materials, there is a continued need to develop new, safe and effective release retarding matrix materials and formulas for preparing simple monolithic matrix tablets for controlled release. The sustained release formulations of the present invention represent a significant improvement over existing drug forms.

Granule Ingredients

Metoprolol

Metoprolol is a cardioselective adrenoceptor blocker. It reduces oxygen use by the heart, slowing the heart rate and reducing cardiac output. It reduces systolic blood pressure and can also be used in the treatment of headache. The present invention is directed in part to sustained release oral dosage forms comprising the succinate salt of metoprolol in a controlled, sustained release formulation. The sustained release oral dosage forms provide beneficial properties including pharmacokinetic parameters. In a preferred embodiment of the present invention, the sustained release excipients are incorporated into a monolithic matrix with the metoprolol succinate which provides for the sustained release of the metoprolol succinate.

Starch Acetate

A key aspect of this invention is its unique combination of rate controlling polymers and modified starch which is acid digestion resistant and remains undigested in the acidic region of stomach and intestine so that it holds the drug content and prevents dose dumping in the human body. The drug is instead released in the colon due to digestion of starch acetate by colonic bacteria and this unique delivery system helps to prevent dose dumping in presence or absence of food in stomach.

Starch acetate as a rate controlling polymer has recently been studied but the specific combination of pregelatinized starch acetate with rate controlling polymers of the present invention allow a once a day drug delivery system of metoprolol succinate in a monolithic matrix tablet to simply and cost effectively achieve bioequivalence with the multiple units particulate systems currently employed.

Starch is a natural polymer which possesses many unique properties. Some synthetic polymers are biodegradable and can be tailor-made easily. Therefore, by combining the individual advantages of starch and polymers, starch-based completely biodegradable polymers are useful for the present invention.

Starches are also used in the food manufacturing industry for processing, and as food thickeners or stabilizers. There are many other diverse uses for starches in the manufacturing industry.

Starch is regenerated from carbon dioxide and water by photosynthesis in plants. Owing to its complete biodegradability, low cost and renewability, starch is considered as a promising candidate for developing sustainable materials. In view of this, starch has been receiving growing attention since the 1970s. Only in the last few years has starch received attention by drug formulators.

Starch is mainly composed of two homopolymers of D-glucose: amylase, a mostly linear $\alpha$-D(1, 4')-glucan and branched amylopectin, having the same backbone structure as amylose but with many $\alpha$-1, 6'-linked branch points. Starch chains have a lot of hydroxyl groups, including two secondary hydroxyl groups at C-2 and C-3 of each glucose residue, as well as one primary hydroxyl group at C-6 when it is not linked. The available hydroxyl groups react with alcohols: they can be oxidized and reduced, and may participate in the formation of hydrogen bonds, ethers and esters.

Starch has different proportions of amylose and amylopectin ranging from about 10-20% amylose and 80-90% amylopectin depending on the source. Amylose is soluble in water and forms a helical structure. Starch occurs naturally as discrete granules since the short branched amylopectin chains are able to form helical structures which crystallize. Starch granules exhibit hydrophilic properties and strong inter-molecular association via hydrogen bonding formed by the hydroxyl groups on the granule surface.

Starches are used in the pharmaceutical industry for a variety of uses, such as an excipient, a tablet and capsule diluent, a tablet and capsule disintegrant, a glidant, or as binder. Starches also absorb water rapidly, allowing tablets to disintegrate appropriately. Dave R H. Overview of pharmaceutical excipients used in tablets and capsules. Drug Topics (online). Advanstar. Oct. 24, 2008 http://drugtopics.modernmedicine.com/drugtopics/Top+News/Overview-of-pharmaceutical-excipients-used-in-tabl/ArticleStandard/Article/detail/561047.

Modified starches have been used for various pharmaceutical purposes such as fillers, superdisintegrants and matrix formers in capsules and tablet formulations. Starch-based biodegradable polymers, in the form of microsphere or hydrogel, are suitable for drug delivery. Crosslinked starch glycolate (sodium salt) is an anionic polymer and produced by crosslinking and carboxymethylation of potato starch. In contrast to the starch of the present invention, in the state of the pharmaceutical art, the sodium starch glycolate from potato is preferred. Crosslinked starch glycolate is used in more than 155 drugs in the US market including Primojel® (DMV-Fonterra) Acyclovir (Zovirax®); theophylline (Theo-Dur®); diltiazem (Cardizem® LA); cimetidine (Tagamet®); fenofibrate (Lipofen®); metoprolol tartrate (Lopressor®) H. Omidian and K. Park in Juergen Siepmann I Ronald A. Siegel Michael J. Rathbone Editors Fundamentals and Applications of Controlled Release Drug Delivery.

Raw starch does not form a paste with cold water and therefore requires cooking if it is to be used as a food thickening agent. Pregelatinized starch, mostly from maize, has been cooked and dried. Pregelatinized starches are highly digestible. Used in instant puddings, pie fillings, soup mixes, salad dressings, sugar confectionery, and as a binder in meat products. Nutritional value is the same as that of the original starch. The result is a multipurpose excipient combining the dilution and disintegration power of native starch with new functionalities, such as flowability and controlled cohesive power. Pregelatinized starches are preferred for the present invention. David A Bender. Starch, Pregelatinized. A Dictionary of Food and Nutrition. 2005. Retrieved from Encyclopedia.com.

One of the important modifications of starch is acetylated starch. Starch acetate has excellent bond forming ability and has been used in the food industry extensively. One method of synthesizing starch acetate is to mix and reflux for 5 h at 150° C. plant starch, excess acetic anhydride and sodium hydroxide 50% solution. The reaction mixture is added to cold water to precipitate the starch acetate formed. The product is collected by vacuum filtration, washed repeatedly with water and dried at 80° C. for 2 h. Starch acetate may be characterized by determining the extent of acetylation and degree of substitution and by IR spectra. Solubility characteristics may also be tested.

Recently, starch acetate was synthesized, characterized and evaluated as rate controlling matrix former for controlled release nifedipine. Matrix tablets of nifedipine were formulated employing starch acetate in different proportions of drug and polymer and the tablets were evaluated for drug release kinetics and mechanism. Nifedipine is an effective and widely prescribed antianginal drug that requires controlled release owing to its short biological half life of 2.5 h. A few sustained release formulations of nifedipine are available commercially. Starch acetate was found suitable as matrix former for controlled release and the matrix tablets of nifedipine formulated employing starch acetate gave controlled release of nifedipine over 24 h and fulfilled the official release specification of nifedipine extended release tablets. Synthesis, Characterization And Evaluation Of Starch Acetate As Rate Controlling Matrix Former For Controlled Release Of Nifedipine Chowdary and Radha *Int. J. Chem. Sci.*: 9(2), 2011, 449-456

Starch acetate is insoluble in water, aqueous buffers of pH 1.2 and 7.4, methanol, petroleum ether, dichloromethane and cyclohexane. It is freely soluble in chloroform.

Starch acetates have mostly been investigated as film-forming coatings using starch acetates (DS 2.8) in combination with commonly used plasticizers on the physical properties of starch acetate films have been evaluated. Starch acetate films are tougher and stronger than ethylcellulose films at the same plasticizer concentration. Also, in most cases, the water vapor permeability of starch acetate films was lower than that of ethylcellulose films. Due to the good mechanical properties, low water vapor, and drug permeabilities of the films, starch acetate seems to be a promising film-former for pharmaceutical coatings. The toughness of the films may result from their dense film structure, which is due to strong interaction forces between adjacent SA molecular chains. J Pharm Sci. 2002 January; 91(1):282-9. Starch acetate—a novel film-forming polymer for pharmaceutical coatings. Tarvainen M, Sutinen R, Peltonen S, Tiihonen P, Paronen P.

Deformation during powder volume reduction, strain-rate sensitivity, intrinsic elasticity of the materials, and tensile strength of the tablets have been examined with the use of starch acetate powders as tablet excipients. Starch acetate with the lowest degree of substitution (ds) still possessed characteristics of native starch granules. The properties of more highly substituted starch acetates depend on precipitation and drying processes. The acetate moiety, perhaps in combination with existing hydroxyl groups, is an effective bond-forming substituent. The formation of strong molecular bonds leads to a very firm and intact tablet structure. Some fragmentation is induced by the slightly harder and more irregular shape of high-substituted starch acetate particles. The plastic flow under compression is enhanced. Acetylated material are slightly less sensitive to fast elastic recovery in-die, but somewhat more elastic out-of-die. In spite of their superior bonding, starch acetates under compression behave similarly to native starches. Drug Dev Ind Pharm. 2002; 28(2):165-75. Acetylation enhances the tabletting properties of starch. Raatikainen P, Korhonen O, Peltonen S, Parone P.

Agglomeration of powders containing starch acetate prior to tablet compression allows for modification and control of the release rate of the drugs from the starch acetate matrix tablets as well as the tensile strength of the tablets. J Pharm Sci. 2007 February; 96(2):438-47. Modifying drug release and tablet properties of starch acetate tablets by dry powder agglomeration. Mäki R, Suihko E, Rost S, Heiskanen M, Murtomaa M, Lehto V P, Ketolainen J.

Other Granule Excipients

Lactose is a milk sugar. It is a disaccharide composed of one galactose and one glucose molecule. In the pharmaceutical industry, lactose is used to help form tablets because it has excellent compressibility properties. It is also used to form a diluent powder for dry-powder inhalations. Lactose may be listed as lactose hydrous, lactose anhydrous, lactose monohydrate, or lactose spray-dried.

Various calcium phosphates are used as diluents in the pharmaceutical industry. Diluents are added to pharmaceutical tablets or capsules to make the product large enough for swallowing and handling, and more stable. Some calcium phosphate salts can be anhydrous, meaning the water has been removed from the salt form. Other calcium phosphates are termed dibasic, meaning they have two replaceable hydrogen atoms.

Hydroxypropyl cellulose (HPC) is a nonionic polymer, being a partially substituted poly (hydroxypropyl) ether of cellulose. It is available in different grades with differing solution viscosities. Molecular weight ranges from ~80,000 to 1,150,000. High viscosity grades of HPC are generally used. Inclusion levels can vary from 15 to 40%. Addition of an anionic surfactant (e.g., sodium lauryl sulfate) reportedly increases HPC viscosity and as a consequence reduces drug release rate. Combinations of HPC and other cellulosic polymers have been used to improve wet granulation and tableting characteristics and better control of drug release. HPC is thermoplastic and its presence may enable processing of HPMC containing formulations using hot melt extrusion or injection molding. It is not widely used because of its low swelling capacity and sensitivity to ionic strength of the dissolution media. Gel strengths of HPC matrices decrease during dissolution, leading to less cohesive gel structures. The lower tablet gel strength of HPC matrices, compared to HPMC can cause poor in vitro/in vivo correlation.

Hydroxyethyl cellulose (HEC) is also a nonionic, partially substituted poly (hydroxyethyl) ether of cellulose. It is available in several grades from Ashland Aqualon Functional Ingredients under the brand name of Natrosol®. These vary in viscosity and degree of substitution. High viscosity grades of HEC (1,500-5,500 mPa of 1% solution) are sometimes used in extended release formulations. Typical inclusion levels are 15-40% of the total formulation mass. However, it may be used in much lower levels such as the 2-3% used in the formulation of Example 1 of this invention. Swelling of HEC matrices has been reported to be considerably greater than HPC matrices. HEC matrices also exhibited relatively higher erosion rates, t50% (time to 50% release) being shorter for HEC than for HPC matrices.

ExtraGranular Excipients

Gelling Agents

A carbomer is a homopolymer of acrylic acid, which is cross-linked, or bonded, with any of several polyalcohol allyl ethers. Carbomer is a generic name for synthetic high molecular weight polymers of acrylic acid. They may be homopolymers of acrylic acid, crosslinked with an allyl etherpentaerythritol, allyl ether of sucrose or allyl ether of propylene. In a water solution at neutral pH, carbomer is an anionic polymer. This makes carbomers polyelectrolytes, with the ability to absorb and retain water and swell to many times their original volume.

Poly acrylic acid and its derivatives are used in disposable diapers, ion exchange resins and adhesives. They are also popular as thickening, dispersing, suspending and emulsifying agents in pharmaceuticals, cosmetics and paints. Usually appearing as a white powder, the compound is used as a thickener and emulsion stabilizer. Best known for its use in the cosmetic industry, it also has practical applications in medicine and hygiene. wikipedia.com and wisegeek.com.

Similar to other polymers, carbomers are made of long chains of many smaller, repeating molecules, which have a large number of bonds. Although the molecular weight varies based on the exact molecules found in the chain, it typically is relatively high. These compounds are capable of absorbing large amounts of water, increasing in volume up to 1,000 times in some cases, so they can form gels and thick solutions that are stable and resistant to spoilage.

Scientists are able to make different types of carbomers, each of which has a slightly different molecular structure. To keep these different kinds straight, they use a numerical suffix and capitalize the word as in a proper title or name, such as Carbomer 940. Under this labeling system, the number indicates the average molecular weight of the polymer chains.

Carbomers are available from Lubrizol under the brand name of Carbopol® and are available in grades that vary in viscosity, polymer type, and polymerization solvent. Being cross-linked, these polymers are not water soluble but are swellable and gel forming. Swelling and gel formation behaviors differ somewhat from other hydrophilic polymers like HPMC, where swelling follows polymer hydration, leading to relaxation of polymer chains and their subsequent entanglement (physical crosslinking) to form a viscous gel. With acrylic acid polymers, surface gel formation is not due to polymer chain entanglement (the polymers are already cross-linked) but to formation of discrete micro gels comprising many polymer particles. Erosion, as occurs with linear polymers like HPMC does not occur because of the water insolubility. Instead, when the hydrogel is fully hydrated, osmotic pressure from within breaks up the structure, sloughing off discrete pieces of the hydrogel. The hydrogel remains intact and drug continues to diffuse uniformly through the gel layer.

In contrast to the situation with linear polymers, higher viscosity does not result in slower drug release with cross-linked polymers. Lightly cross-linked polymers (lower viscosity) are generally more efficient in controlling release than highly cross-linked variants. Release from carbomer matrices may depend on the pH of dissolution media, because of the anionic nature of the polymer (pKa 6±0.5). Swelling and gel formation are pH dependent. At lower pH the polymer is not fully swollen and drug release is faster. As pH increases the polymer swells and rapidly forms a gel layer, prolonging drug release. Carbomers, being anionic may form complexes with cationic drugs depending on drug properties such as pKa, solubility, amine group strength, steric orientation, molecular weight and size.

It has been reported that carbomer inclusion levels of about 30% produce comparable drug release profiles to HPMC in both water and 0.1 N HCl. Release was slower in pH 6.8 phosphate buffer. Carbomer matrices also exhibited significantly lower gel strengths compared to HPMC matrices in all three media. This has been postulated as the reason for their significantly faster drug release in vivo compared to HPMC matrices. 7 Drug-Polymer Matrices for Extended Release 143

Polyethylene oxide (PEO) [POLYOX™] resins are water soluble, nonionic polymers manufactured by Dow Chemical Company. They are free flowing white powders, soluble in water at temperatures up to 98° C. and in certain organic solvents. Structures comprise the repeating sequence—(CH2CH2O)n where n represents the average number of oxyethylene groups. It is highly crystalline and available in molecular weight grades ranging from $1 \times 10^5$ to $7 \times 10^6$ Da. Their high molecular weights mean that the concentration of reactive end groups is very low. However, as their paired ether-oxygen electrons have a strong affinity for hydrogen bonding, they can form association complexes with a variety of monomeric and polymeric electron acceptors (e.g., gelatin, carbomer) as well as certain inorganic electrolytes, e.g., alkali halides. These water-soluble resins have applications in pharmaceutical products, such as in controlled release solid dose matrix systems, tablet binding, tablet coatings, transdermal drug delivery systems, and mucosal bioadhesives and gastro-retentive dosage forms. They exhibit film forming and water retention properties. It has high water solubility and low toxicity. http://www.pharmainfo.net/reviews/polyox-polyethylene-oxide-applications-pharma-industry. Submitted by Saritha R Bhandary on Wed, Sep. 22, 2010—22:38

PEO resins are among the fastest hydrating water soluble polymers, quickly forming hydrogels that initiate and regulate drug release. Systems using such resins are often superior in approaching zero-order release profiles. PEO is generally used at 20-90% inclusion level depending on the drug and the desired release characteristics, however, in the instant invention levels of 10% and less are used.

PEO behaves similarly to HPMC in hydrophilic matrix systems. With appropriate selection of a suitable viscosity grade, one is able to achieve release profiles similar to hypromellose matrices. Grades available are POLYOX WSR-205 NF, WSR-1105 NF, WSR N-12 K NF, WSR N-60 K NF, WSR-301 NF, WSR-303 NF, and WSR Coagulant NF. The high swelling capacity of PEO has been used in hydrophilic matrices to achieve expanded swelling, providing enhanced gastroretention.

A formulation of gabapentin containing PEO and HPMC exhibited significant matrix swelling and gastric retention. 7 Drug-Polymer Matrices for Extended Release 145

Several other materials can be useful gel matrix formers. They include methylcellulose, guar gum, chitosan, and cross-linked high amylose starch.

Hydroxypropyl methylcellulose (HPMC or hypromellose) is a semisynthetic, inert, viscoelastic polymer used as an ophthalmic lubricant, as well as an excipient and controlled-delivery component in oral medicaments, found in a variety of commercial products. Hypromellose is a solid, and is a slightly off-white to beige powder in appearance and may be formed into granules. The compound forms colloids when dissolved in water. Wikipedia.com. It is widely used in matrix applications. Key advantages include global regulatory acceptance, stability, nonionic nature (resulting in pH-independent release of drugs), and ease of processing by direct compression (DC) or granulation. Other advantages are versatility and suitability for various drugs and release profiles (different viscosity grades being available) and extensive history of use. It is a mixed alkyl hydroxyalkyl cellulose ether containing methoxyl and hydroxypropyl groups. Type and distribution of the substituent groups affect physicochemical properties such as rate and extent of hydration, surface activity, biodegradation, and mechanical plasticity. Matrices exhibit pH-independent drug release profiles while aqueous solutions are stable over a wide pH range and are resistant to enzymatic degradation. Controlled Release in Oral Drug Delivery Clive G. Wilson Crowly Springer 2011 Chapter 7Drug-Polymer Matrices for Extended Release Sandip B. Tiwari, James DiNunzio, and Ali Rajabi-Siahboomi.

The first two digits represent the mean % methoxyl substitution and the last two the mean % hydroxypropyl substitution. HPMC is highly hydrophilic, hydrating rapidly in contact with water. Since the hydroxypropyl group is hydrophilic and the methoxyl group is hydrophobic, the ratio of hydroxypropyl to methoxyl content influences water mobility in a hydrated gel layer and therefore, drug release. Grades for extended release matrix formulations include E50LV, K100LV CR, K4M CR, K15M CR, K100M CR, E4M CR, and E10M CR. Viscosities of 2% aqueous solutions of these polymers range from 50 to 100,000 cPs at 20° C. Inclusion level can vary from 10 to 80% dosage form.

Hypromellose in an aqueous solution, unlike methylcellulose, exhibits a thermal gelation property. That is, when the solution heats up to a critical temperature, the solution congeals into a non-flowable but semi-flexible mass. Typically, this critical (congealing) temperature is inversely related to both the solution concentration of HPMC and the concentration of the methoxy group within the HPMC molecule (which in turn depends on both the degree of substitution of the methoxy group and the molar substitution. That is, the higher the concentration of the methoxy group, the lower the critical temperature. The inflexibility/viscosity of the resulting mass, however, is directly related to the concentration of the methoxy group (the higher the concentration, the more viscous or less flexible the resulting mass is).

In addition to its use in ophthalmic liquids, hypromellose can be used as an excipient in oral tablet and capsule formulations, where, depending on the grade, it functions as controlled release agent to delay the release of a medicinal compound into the digestive tract. It is also used as a binder and as a component of tablet coatings.

Polymethacrylates are synthetic cationic or anionic polymers of dimethylaminoethyl methacrylates, methacrylic acid, and methacrylic acid esters in varying ratios. Methacrylic acid is a colourless, viscous organic acid with an acrid unpleasant odor. It is soluble in warm water and miscible with most organic solvents. Methacrylic acid is produced industrially on a large scale as a precursor to its esters, especially methyl methacrylate (MMA) and poly (methyl methacrylate) (PMMA). The methacrylates have numerous uses, most notably in the manufacture of polymers with trade names such as Lucite and Plexiglas. MAA occurs naturally in small amounts in the oil of Roman chamomile. Several types are commercially available (Eudragits®, Evonik) for use in drug formulations as dry powders and aqueous dosage forms. Polymethacrylates can be used as binders for both aqueous and organic solvent granulation, forming matrices with extended release characteristics. In general, greater polymer inclusion levels (5-20%) are used to control release from matrices. Drug release may also be affected by pH of the dissolution medium. Wiki.

Lubricants

Magnesium stearate is used as an anti-adherent and it has lubricating properties, preventing the ingredients from sticking to manufacturing equipment during the compression of powders into solid tablets. Magnesium stearate may also affect the release time of the metoprolol in the tablets.

Coating

Opadry is A one-step film coating system which combines polymer, plasticizer and pigment. Opadry film coating results in attractive, elegant coatings that can be easily dispersed in aqueous or organic solvent solutions. Opadry results in the elimination of separate inventories of polymer, plasticizer and pigment and reduces batch-to-batch color inconsistency.

EXAMPLES

The following examples illustrate various aspects of the present invention. They are not to be construed to limit the claims in any manner whatsoever.

Example 1

In this example, sustained release metoprolol succinate in accordance with the present invention is prepared having the formula listed in Table 1:

TABLE 1

| Item No. | Ingredient | Function | 100 mg Mg/tab | 100 mg % w/w | 200 mg Mg/tab | 200 mg % w/w |
|---|---|---|---|---|---|---|
| | | DRY MIXING: | | | | |
| 1 | Metoprolol Succinate, USP | API | 95.00 | 24.55 | 190.00 | 24.55 |
| 2 | Dibasic Calcium Phosphate Dihydrate (Emcompress ® Premium), NF | Pharmaceutical excipient Diluent | 30.00 | 7.75 | 60.00 | 7.75 |
| 3 | Lactose Monohydrate (Granulac-200), NF | Pharmaceutical excipient Diluent | 30.00 | 7.75 | 60.00 | 7.75 |
| 4 | Pregelatinized Modified Starch (Amprac-01), NF | Binder cum Release controlling agent | 30.00 | 7.75 | 60.00 | 7.75 |
| 5 | Hydroxy Ethyl Cellulose (Natrosol ® 250 HHX Pharm), NF | Binder cum Release controlling agent | 10.00 | 2.58 | 20.00 | 2.58 |
| | | GRANULATION: | | | | |
| 6 | Purified Water# | | q.s. | — | q.s. | — |
| | | EXTRAGRANULAR: | | | | |
| 7 | Carbomer Homopolymer, Type A (Carbopol ® 71 G Polymer), NF | Release controlling agent | 43.00 | 11.11 | 86.00 | 11.11 |
| 8 | Polyethylene Oxide (Sentry (TM) Polyox (TM) WSR Coagulant-Leo), NF | Release controlling agent | 38.50 | 9.95 | 77.00 | 9.95 |
| 9 | Hypromellose (Benecel ® K200M PH CR), NF | Release controlling agent | 55.00 | 14.21 | 110.00 | 14.21 |
| 10 | Methacrylic Acid Copolymer, Type C (Eudragit ® L 100-55), NF | Release controlling agent | 33.50 | 8.66 | 67.00 | 8.66 |
| | | LUBRICATION: | | | | |
| 11 | Magnesium Stearate, NF | Lubricant | 10.00 | 2.58 | 20.00 | 2.58 |
| | TOTAL | | 375.00 | — | 750.00 | — |
| 12 | Opadry II White (85F18422), INH | Film Coating Material | 12.00 | 3.10 | 24.00 | 3.10 |
| 13 | Purified Water#, USP | Coating Solvent | q.s | — | q.s | — |
| | TOTAL | | 387.00 | 100.00 | 774.00 | 100.00 |

Drug formulations of the present invention are prepared as follows:

Granulating: the metoprolol succinate is blended with hydroxy ethyl cellulose, dicalcium phosphate, lactose monohydrate and pregelatinized starch acetate in a high shear granulator. The mixture is then granulated in hot water and dry mixed with the granulator and impeller set at slow speed. With the granulator and impeller set a slow speed, purified water is added to the mixed powders and granulated with the granulator and impeller set at slow speed.

Drying: The wet granulation is transferred to a fluid bed dryer and dried.

Mixing and tableting: After being dried in a fluid bed dryer, the granules thus formed are mixed with carbomer homopolymer, polyethylene oxide, hypromellose, methacrylic acid copolymer.

Coating: Finally, the tablets are coated with Opadry II White and other coating agents (e.g., talc and titanium dioxide) to produce the final formulation. The tablet granules were compressed into tablets on a tablet punching machine.

Example 2. Bioequivalence Clinical Trial of Drug Produced in Example 1

OPEN LABEL, BALANCED, RANDOMIZED, TWO-TREATMENT, TWO-SEQUENCE, TWO-PERIOD, SINGLE ORAL DOSE, TWO-WAY CROSSOVER BIOEQUIVALENCE STUDY OF METOPROLOL SUCCINATE EXTENDED RELEASE TABLET 200 mg WITH TOPROL-XL® (METOPROLOL SUCCINATE) EXTENDED RELEASE TABLETS 200 mg AS REFERENCE FORMULATION IN HEALTHY, ADULT, HUMAN MALE AND FEMALE SUBJECTS UNDER FASTING CONDITION

Objectives:

The objectives of the study were to assess the bioequivalence of single oral dose of Metoprolol Succinate Extended Release Tablet 200 mg of the invention as test formulation and Toprol-XL® (metoprolol succinate) Extended Release Tablet 200 mg as reference formulation in healthy, adult, human male and female subjects under fasting condition and to monitor the safety profile and tolerability of the study medication in the subjects.

Methodology:

Number of Subjects:

One hundred and twenty three (123) volunteers were screened. Out of one hundred and twenty three (123) screened volunteers, one hundred and one (101) volunteers were considered eligible as per protocol. Out of one hundred and one (101) eligible volunteers, twenty (20) subjects were enrolled on check-in day of period I of cohort I and seventy six (76) subjects were enrolled on the check-in day of period I of cohort II Dosing:

A single oral dose of one extended release tablet of either the test formulation (Test A) or the reference formulation (Reference B), both containing Metoprolol succinate 190 mg, was administered along with 240±2 mL drinking water at room temperature as per the randomisation schedule in the morning under fasting condition (fasting at least 10.0 hours) during both the periods of both the cohorts (except discontinued subjects). Subjects were instructed not to chew or crush the tablet but to consume it as a whole. Dosing activity was supervised by Clinical Sub-Investigator and QC person of clinical department. Subjects seated upright for dose administration. At the end of the study, each subject had received both the formulations once (except discontinued subjects).

PK Blood Draw Time Points:

During each study period, 23 PK blood samples (5 mL each) were collected from each subject at the following time points: at pre-dose (within 1.0 hour prior to dosing) and at 1.0, 1.5, 2.0, 2.5, 3.0, 3.5, 4.0, 4.5, 5.0, 5.5, 6.0, 6.5, 7.0, 7.5, 8.0, 9.0, 10.0, 12.0, 16.0, 24.0, 36.0 and 48.0 hours post-dose (except for subjects who did not turn up for ambulatory samples and for discontinued subjects).

Diet:

Dinner was provided on check-in day of both the periods of both the cohorts. Subjects fasted overnight (at least 10 hours) before dosing during both the periods of both the cohorts (except for discontinued subjects). Food was not allowed for at least 4.0 hours post-dose. Standard meal/snacks were provided approximately at 4.0, 8.0, 12.0 and 24.0 hours post dose during both the periods of both the cohorts (except for discontinued subjects).

Clinical Stay:

Subjects were admitted and housed in the clinical facility before 20.0 to 11.5 hours of dosing and remained housed until the 24.0 hours post dose PK blood draw during both the periods of both the cohorts (except for discontinued subjects). Subjects came to Synchron Research Services Pvt. Ltd., clinical facility for ambulatory PK blood samples for 36.0 and 48.0 hours post dose (except for subjects who did not turn up for ambulatory samples and for discontinued subjects).

Washout Period:

There was a washout period of 7 days between both consecutive dosings of both the cohorts.

Bioanalytical Procedures:

Metoprolol in human plasma were estimated by using a validated LCMS/MS method. LLOQ of Metoprolol is 0.504 ng/mL. Range of standard curve concentration for Metoprolol is 0.504 to 125.963 ng/mL. For details refer Volume II, bioanalytical report.

Number of Subjects (Planned and Analyzed):

There were ninety six (96) subjects planned in the study. All ninety six (96) were enrolled in two cohorts in the study. Out of ninety six (96) subjects, eighty three (83) subjects completed the study. Hence, pharmacokinetic and statistical analysis for Test A and Reference B were performed for eighty three (83) subjects.

Safety assessment was done for all ninety six (96) subjects.

Main Criteria for Inclusion:

Healthy human volunteers of any race within the age range of 18 to 45 years, inclusive.

Test Product/Investigational Product, Batch Number and Mode of Administration:

Metoprolol Succinate Extended Release Tablet 200 mg

Each white to off white, oval shaped, biconvex, coated tablets, debossed with "AN 344" on one side and scoring on other side, contains Metoprolol succinate 190 mg equivalent to 200 mg Metoprolol tartrate, USP.

Reference Product/Investigational Product, Batch Number and Mode of Administration:

Toprol-XL® (Metoprolol Succinate extended release tablets) 200 mg

Each white, oval shaped, biconvex, film coated scored tablets, engraved with "A/my", contains Metoprolol succinate 190 mg equivalent to 200 mg Metoprolol tartrate, USP.

Criteria for Evaluation:

There were ninety six (96) subjects planned in the study. All ninety six (96) subjects were enrolled in two cohorts in the study. Out of ninety six (96) subjects, eighty three (83) subjects completed the study. Hence, pharmacokinetic and statistical analysis for Test A and Reference B were performed for eighty three (83) subjects.

Safety assessment was done for all ninety six (96) subjects.

Pharmacokinetics (PK):

The following pharmacokinetic parameters were calculated for Metoprolol.

$C_{max}$, $AUC_{(0-t)}$, $AUC_{(0-\infty)}$, % $AUC_{extra}$, $T_{max}$, $K_{el}$ ($\lambda_z$) and $t_{1/2}$.

Safety:

The incidences of all adverse events (AEs) are tabulated by treatment and subject number. Absolute values for laboratory parameters are documented and values outside their respective normal ranges are flagged.

Statistical Methods:

Using General Linear Model (GLM) procedures in Statistical Analysis System (SAS), analysis of variance (ANOVA) was performed on ln-transformed $C_{max}$, $AUC_{(0-t)}$ and $AUC_{(0-\infty)}$ for Metoprolol at the significance level of 0.05 for period and sequence. The 90% confidence interval (90% C.I.) for the ratio "Test/Reference" was calculated based on the difference in the Least Squares Means from the ANOVA of $AUC_{(0-t)}$, $AUC_{(0-\infty)}$ and $C_{max}$ for Metoprolol. Since, the study was conducted in two cohorts, additional test to see the cohort effect was performed using ANOVA. (Refer Appendix 16.2.2.1)

TABLE 2

Pharmacokinetic Results:

Mean Pharmacokinetic parameters of Metoprolol after oral administration of Metoprolol Succinate Extended Release Tablet 200 mg (Test formulation A) and Toprol-XL ® (Metoprolol succinate extended release tablets) 200 mg (Reference formulation B) under fasting condition:

| Pharmacokinetic Parameters | Geometric Mean (% CV) Arithmetic Mean ± SD | |
|---|---|---|
| | Test Formulation (A) (n = 83) | Reference Formulation (B) (n = 83) |
| $C_{max}$ (ng/mL) | 43.606 (48.80) | 42.381 (49.30) |
| | 49.037 ± 23.928 | 47.290 ± 23.315 |
| $T_{max}$ (h)* | 7.50 (3.00-16.00) | 9.00 (2.00-16.00) |
| $AUC_{(0-t)}$ | 736.388 (68.38) | 728.621 (74.64) |
| (ng · h/mL) | 910.344 ± 622.491 | 906.128 ± 676.371 |
| $AUC_{(0-\infty)}$ | 785.599 (69.60)** | 767.120 (76.38)*** |
| (ng · h/mL) | 972.544 ± 676.866 | 962.525 ± 735.178 |
| $K_{el}$ ($\lambda_z$) (1/h) | 0.13062 (29.02)** | 0.12831 (27.40)*** |
| | 0.13902 ±0.04034 | 0.13372 ± 0.03663 |
| $t_{1/2}$ (h) | 5.31 (65.60)** | 5.40 (39.78)*** |
| | 5.92 ± 3.88 | 5.70 ± 2.27 |
| % $AUC_{extra}$ | 1.80 (211.20)** | 1.78 (167.93)*** |
| | 4.95 ± 10.45 | 3.58 ± 6.02 |

*median (min-max),

**n = 72,

***n = 74 as in rest of the subjects, clear elimination phase was not seen or as per our SOP we require minimum 3 time points (Excluding $C_{max}$) in the apparent elimination phase for the calculation of elimination rate constant. However, in some subjects, it was not possible to get 3 time points excluding $C_{max}$ in the apparent elimination phase. Hence, $\lambda_z$ ($K_{el}$), $t_{1/2}$, $AUC_{(0-\infty)}$ and % $AUC_{extra}$ could not be calculated.

*median (min-max),

**n = 34 as clear elimination phase was not seen in one subject (subject No.17)

TABLE 3

Relative bioavailability assessments for S-Etodolac after oral administration of Metoprolol Succinate Extended Release Tablet 200 mg (Test formulation A) and TOPROL-XL ® ( Metoprolol Succinate extended release tablets) 50 mg (Reference formulation B) under fasting condition:

| | Ratio, 90% Confidence Intervals, and Intra-subject Variability (n = 35) | | |
|---|---|---|---|
| Pharmacokinetic Parameters | Ratio of Geometric Means (%) | 90% C.I. | Intra-Subject % CV |
| $AUC_{(0-t)}$ | 99.79% | 94.27% to 105.64% | 14.15% |
| $AUC_{(0-\infty)}$* | 98.98% | 93.52% to 104.77% | 13.88% |
| $C_{max}$ | 108.60% | 97.93% to 120.44% | 26.00% |

*n = 34 as clear elimination phase was not seen in one subject (subject No.17)

TABLE 4

Relative bioavailability assessments for Metoprolol after oral administration of Metoprolol Succinate Extended Release Tablet 200 mg (Test formulation A) and Toprol-XL ®( Metoprolol succinate extended release tablets) 200 mg (Reference formulation B) under fasting condition:

Ratio, 90% Confidence Intervals, and Intra-subject Variability (n = 83)

| Pharmacokinetic Parameters | Ratio of Geometric Means (%) | 90% C.I. | Intra-Subject % CV |
|---|---|---|---|
| $AUC_{(0-t)}$ | 100.95% | 93.42% to 109.09% | 30.71% |
| $AUC_{(0-\infty)}$* | 101.70% | 92.43% to 111.91% | 33.09% |
| $C_{max}$ | 111.90% | 105.07% to 119.17% | 19.84% |

*no. of subjects taken into calculation = 64 as for remaining subjects, clear elimination phase was not seen or it was not possible to get 3 time points excluding $C_{max}$ in the apparent elimination phase either in test or reference formulation. Hence, $AUC_{(0-\infty)}$ could not be calculated.

Conclusions:

Pharmacokinetic & Statistical:

The statistical results indicated that "test/reference" ratio (Test A vs. Reference B) of geometric means for $AUC_{(0-t)}$, $AUC_{(0-\infty)}$ and $C_{max}$ were 100.95%, 101.70% and 111.90% respectively, which lie within the bioequivalence range 80.00% to 125.00% for Metoprolol.

The 90% confidence intervals for $AUC_{(0-t)}$, $AUC_{(0-\infty)}$ and $C_{max}$ were 93.42% to 109.09%, 92.43% to 111.91% and 105.07% to 119.17% respectively, which lie within the bioequivalence range 80.00% to 125.00% for Metoprolol.

As 90% confidence intervals and "test/reference" ratio of geometric means are within the bioequivalence range of 80.00% to 125.00% for $AUC_{(0-t)}$, $AUC_{(0-\infty)}$ and $C_{max}$, it can be concluded that Metoprolol Succinate Extended Release Tablet 200 mg (Test formulation A) is bioequivalent to Toprol-XL® (Metoprolol Succinate extended release tablets) 200 mg (Reference formulation B) under fasting condition.

Example 3. Bioequivalence Clinical Trial of Drug Produced According to the Invention Title of Study:

OPEN LABEL, BALANCED, RANDOMIZED, TWO-TREATMENT, TWO-SEQUENCE, TWO-PERIOD, SINGLE ORAL DOSE, TWO-WAY CROSSOVER BIOEQUIVALENCE STUDY OF METOPROLOL SUCCINATE EXTENDED RELEASE TABLET 50 mg WITH TOPROL-XL® (METOPROLOL SUCCINATE) EXTENDED RELEASE TABLETS 50 mg AS REFERENCE FORMULATION IN HEALTHY, ADULT, HUMAN MALE AND FEMALE SUBJECTS UNDER FASTING CONDITION

Objectives:

The objectives of the study were to assess the bioequivalence of single oral dose of Metoprolol Succinate Extended Release Tablet 50 mg as test formulation and Toprol-XL® (metoprolol succinate) Extended Release Tablet 50 mg as reference formulation in healthy, adult, human male and female subjects under fasting condition and to monitor the safety profile and tolerability of the study medication in the subjects.

Methodology:

Number of Subjects:

One hundred and seventy (170) volunteers were screened. Out of one hundred and seventy (170) screened volunteers, one hundred and eleven (111) volunteers were considered eligible as per protocol. Out of one hundred and eleven (111) eligible volunteers, twenty four (24) subjects were enrolled on check-in day of period I of cohort I and seventy two (72) subjects were enrolled on the check-in day of period I of cohort II.

Dosing:

A single oral dose of one extended release tablet of either the test formulation (Test A) or the reference formulation (Reference B), both containing Metoprolol succinate 47.5 mg, was administered along with 240±2 mL drinking water at room temperature as per the randomisation schedule in the morning under fasting condition (fasting at least 10.0 hours) during both the periods of both the cohorts (except discontinued subjects). Subjects were instructed not to chew or crush the tablet but to consume it as a whole. Dosing activity was supervised by Clinical Investigator/Clinical Sub-Investigator/Physician and QC person of clinical department. Subjects seated upright for dose administration. At the end of the study, each subject had received both the formulations once (except discontinued subjects).

PK Blood Draw Time Points:

During each study period, 23 PK blood samples (5 mL each) were collected from each subject at the following time points: at pre-dose (within 1.0 hour prior to dosing) and at 1.0, 1.5, 2.0, 2.5, 3.0, 3.5, 4.0, 4.5, 5.0, 5.5, 6.0, 6.5, 7.0, 7.5, 8.0, 9.0, 10.0, 12.0, 16.0, 24.0, 36.0 and 48.0 hours post-dose (except for subjects who did not turn up for ambulatory samples and for discontinued subjects).

Diet:

Dinner was provided on check-in day of both the periods of both the cohorts. Subjects fasted overnight (at least 10 hours) before dosing during both the periods of both the cohorts (except for discontinued subjects). Food was not allowed for at least 4.0 hours post-dose. Standard meal/snacks were provided approximately at 4.0, 8.0, 12.0 and 24.0 hours post dose during both the periods of both the cohorts (except for discontinued subjects).

Clinical Stay:

Subjects were admitted and housed in the clinical facility before 20.0 to 11.5 hours of dosing and remained housed until the 24.0 hours post dose PK blood draw during both the periods of both the cohorts (except for discontinued subjects). Subjects came to Synchron Research Services Pvt. Ltd., clinical facility for ambulatory PK blood samples for 36.0 and 48.0 hours post dose (except for subjects who did not turn up for ambulatory samples and for discontinued subjects).

There was a washout period of 7 days between both consecutive dosings of both the cohorts.

Bioanalytical Procedures:

Metoprolol in human plasma were estimated by using a validated LCMS/MS method. LLOQ of Metoprolol is 0.500 ng/mL. Range of standard curve concentration for Metoprolol is 0.500 to 40.011 ng/mL. For details refer Volume II, bioanalytical report.

Number of Subjects (Planned and Analyzed):

There were ninety six (96) subjects planned in the study. All ninety six (96) subjects were enrolled in two cohorts in the study. Out of ninety six (96) subjects, ninety (90) subjects completed the study. Hence, pharmacokinetic and statistical analysis for Test A and Reference B were performed for ninety (90) subjects.

Safety assessment was done for all ninety six (96) subjects.

Main Criteria for Inclusion:

Healthy human volunteers of any race within the age range of 18 to 45 years, inclusive.

Test Product/Investigational Product, Batch Number and Mode of Administration:

Metoprolol Succinate Extended Release Tablet 50 mg

Each white to off white, round shaped, biconvex, coated tablets, debossed with "AN 342" on one side and scoring on other side, contains Metoprolol succinate 47.5 mg equivalent to 50 mg Metoprolol tartrate, USP.

Reference Product/Investigational Product, Batch Number and Mode of Administration:

Toprol-XL® (Metoprolol Succinate extended release tablets) 50 mg

Criteria for Evaluation:

There were ninety six (96) subjects planned in the study. All ninety six (96) subjects were enrolled in two cohorts in the study. Out of ninety six (96) subjects, ninety (90) subjects completed the study. Hence, pharmacokinetic and statistical analysis for Test A and Reference B were performed for ninety (90) subjects.

Safety assessment was done for all ninety six (96) subjects.

Pharmacokinetics (PK):

The following pharmacokinetic parameters were calculated for Metoprolol.

$C_{max}$, $AUC_{(0-t)}$, $AUC_{(0-\infty)}$, % $AUC_{extra}$, $T_{max}$, $K_{el}$ ($\lambda_z$) and $t_{1/2}$.

Safety:

The incidences of all adverse events (AEs) are tabulated by treatment and subject number. Absolute values for laboratory parameters are documented and values outside their respective normal ranges are flagged.

Statistical Methods:

Using General Linear Model (GLM) procedures in Statistical Analysis System (SAS), analysis of variance (ANOVA) was performed on ln-transformed $C_{max}$, $AUC_{(0-t)}$ and $AUC_{(0-\infty)}$ for Metoprolol at the significance level of 0.05 for period and sequence. The 90% confidence interval (90% C.I.) for the ratio "Test/Reference" was calculated based on the difference in the Least Squares Means from the ANOVA of $AUC_{(0-t)}$, $AUC_{(0-\infty)}$ and $C_{max}$ for Metoprolol. Since, the study was conducted in two cohorts, additional test to see the cohort effect was performed using ANOVA. (Refer Appendix 16.2.2.1)

TABLE 5

Pharmacokinetic Results:

Mean Pharmacokinetic parameters of Metoprolol after oral administration of Metoprolol Succinate Extended Release Tablet 50 mg (Test formulation A) and Toprol-XL® (Metoprolol succinate extended release tablets) 50 mg (Reference formulation B) under fasting condition:

| Pharmacokinetic Parameters | Test Formulation (A) (n = 90) Geometric Mean (% CV) Arithmetic Mean ±SD | Reference Formulation (B) (n = 90) Geometric Mean (% CV) Arithmetic Mean ±SD |
|---|---|---|
| $C_{max}$ (ng/mL) | 10.775 (54.53) | 9.974 (56.40) |
|  | 12.263 ± 6.687 | 11.449 ± 6.457 |
| $T_{max}$ (h)* | 7.00 (2.00-24.00) | 10.00 (3.50-16.00) |
| $AUC_{(0-t)}$ (ng·h/mL) | 168.244 (71.13) | 185.129 (73.54) |
|  | 207.700 ± 147.728 | 231.030 ± 169.894 |
| $AUC_{(0-\infty)}$ (ng·h/mL) | 193.795 (67.76)** | 212.069 (72.87)*** |
|  | 237.073 ± 160.642 | 260.840 ± 190.085 |
| $K_{el}$ ($\lambda_z$) (1/h) | 0.10519 (38.69)** | 0.09269 (28.62)*** |
|  | 0.11615 ± 0.04494 | 0.09685 ± 0.02772 |
| $t_{1/2}$ (h) | 6.59 (80.99)** | 7.48 (33.99)*** |
|  | 7.73 ± 6.26 | 7.85 ± 2.67 |
| % $AUC_{extra}$ | 5.86 (117.26)** | 6.78 (99.39)*** |
|  | 10.02 ± 11.75 | 11.09 ± 11.02 |

*median (min-max),
**n = 71,
***n = 65 as in rest of the subjects, clear elimination phase was not seen or as per our SOP we require minimum 3 time points (Excluding $C_{max}$) in the apparent elimination phase for the calculation of elimination rate constant. However, in some subjects, it was not possible to get 3 time points excluding $C_{max}$ in the apparent elimination phase. Hence, $\lambda_z$ ($K_{el}$), $t_{1/2}$, $AUC_{(0-\infty)}$ and % $AUC_{extra}$ could not be calculated.

TABLE 6

Relative bioavailability assessments for Metoprolol after oral administration of Metoprolol Succinate Extended Release Tablet 50 mg (Test formulation A) and Toprol-XL® (Metoprololsuccinate extended release tablets) 50 mg (Reference formulation B) under fasting condition:

| Pharmacokinetic Parameters | Ratio, 90% Confidence Intervals, and Intra-subject Variability (n = 90) | | |
|---|---|---|---|
|  | Ratio of Geometric Means (%) | Ratio of Geometric Means (%) | Ratio of Geometric Means (%) |
| $AUC_{(0-t)}$ | 91.15% | 85.28% to 97.43% | 27.36% |
| $AUC_{(0-\infty)}$* | 91.91% | 82.91% to 101.89% | 32.71% |
| $C_{max}$ | 108.26% | 103.21% to 113.57% | 19.48% |

*no. of subjects taken into calculation = 54 as for remaining subjects, clear elimination phase was not seen or it was not possible to get 3 time points excluding $C_{max}$ in the apparent elimination phase either in test or reference formulation. Hence, $AUC_{(0-\infty)}$ could not be calculated.
*median (min-max),
**n = 34 as clear elimination phase was not seen in one subject (subject No.17)

TABLE 7

Relative bioavailability assessments for S-Etodolac after oral administration of Metoprolol Succinate Extended Release Tablet 50 mg (Test formulation A) and TOPROL-XL® (Metoprolol Succinate extended release tablets) 50 mg (Reference formulation B) under fasting condition:

| Pharmacokinetic Parameters | Ratio, 90% Confidence Intervals, and Intra-subject Variability (n = 35) | | |
|---|---|---|---|
|  | Ratio of Geometric Means (%) | 90% C.I. | Intra-Subject % CV |
| $AUC_{(0-t)}$ | 99.79% | 94.27% to 105.64% | 14.15% |
| $AUC_{(0-\infty)}$* | 98.98% | 93.52% to 104.77% | 13.88% |
| $C_{max}$ | 108.60% | 97.93% to 120.44% | 26.00% |

*n = 34 as clear elimination phase was not seen in one subject (subject No.17)

Conclusions:

Pharmacokinetic & Statistical:

The statistical results indicated that "test/reference" ratio (Test A vs. Reference B) of geometric means for $AUC_{(0-t)}$, $AUC_{(0-\infty)}$ and $C_{max}$ were 91.15%, 91.91% and 108.26% respectively, which lie within the bioequivalence range 80.00% to 125.00% for Metoprolol.

The 90% confidence intervals for $AUC_{(0-t)}$, $AUC_{(0-\infty)}$ and $C_{max}$ were 85.28% to 97.43%, 82.91% to 101.89% and 103.21% to 113.57% respectively, which lie within the bioequivalence range 80.00% to 125.00% for Metoprolol.

90% confidence intervals and "test/reference" ratio of geometric means are within the bioequivalence range of 80.00% to 125.00% for $AUC_{(0-t)}$, $AUC_{(0-\infty)}$ and $C_{max}$. Hence, it can be concluded that Metoprolol Succinate Extended Release Tablet 50 mg (Test formulation A) is bioequivalent to Toprol-XL® (Metoprolol Succinate extended release tablets) 50 mg (Reference formulation B) under fasting condition.

What is claimed is:

1. An extended-release drug composition comprising a monolithic matrix tablet comprising metoprolol containing granules and extragranular excipients, wherein the granules comprise about:
   a. 20-30% of a metoprolol salt selected from the group consisting of metoprolol succinate and metoprolol tartrate;
   b. 5-10% pregelatinized starch acetate as a rate-controlling polymer; and
   c. one or more additional granule excipients selected from the group consisting of lactose, calcium phosphate, hydroxypropyl cellulose and hydroxyethyl cellulose; wherein the granule is uncoated; wherein the pregelatinized starch acetate comprises from 10-20% amylose, and from 80-90% amylopectin.

2. The extended-release drug composition of claim 1, wherein the granules further comprise one or more diluents selected from the group consisting of dibasic calcium phosphate and lactose.

3. The extended-release drug composition of claim 1, wherein the granules further comprise hydroxylethyl cellulose.

4. The extended-release drug composition of claim 1, wherein the pregelatinized starch acetate is insoluble in water, aqueous buffers of pH 1.2 and 7.4; methanol; petroleum ether; dichloromethane and cyclohexane.

5. The extended-release drug composition of claim 1, wherein the extragranular excipients comprise one or more of gelling agents, lubricants, and a coating.

6. The extended-release drug composition of claim 5, wherein the extragranular excipients comprise one or more gelling agents.

7. The extended-release drug composition of claim 6, wherein the gelling agent comprises a homopolymer of acrylic acid, cross-linked or bonded with a polyalcohol allyl ether.

8. The extended-release drug composition of claim 1, wherein the extragranular excipients comprise polyethylene oxide.

9. The extended-release drug composition of claim 1, wherein the extragranular excipients comprise one or more of methylcellulose, guar gum, chitosan and cross-linked high amylose starch.

10. The extended-release drug composition of claim 1, wherein the granules further comprise about:
   d. 5-10% dibasic calcium phosphate;
   e. 5-10% lactose monohydrate; and
   f. 1-5% hydroxyl ethyl cellulose;
and where the extragranular excipients comprise:
   g. a release controlling agent.

11. The extended-release drug composition of claim 10, wherein the extragranular excipients further comprise a lubricant.

12. The extended-release drug composition of claim 11, wherein the lubricant is magnesium stearate.

13. The extended-release drug composition of claim 10, wherein the extragranular excipients further comprises a coating agent.

14. The extended-release drug composition of claim 13, wherein the coating agent is a film coating.

* * * * *